(12) United States Patent
Leonhardt

(10) Patent No.: US 6,280,467 B1
(45) Date of Patent: Aug. 28, 2001

(54) DELIVERY SYSTEM FOR DEPLOYMENT AND ENDOVASCULAR ASSEMBLY OF A MULTI-STAGE STENTED GRAFT

(75) Inventor: Howard J. Leonhardt, Davie, FL (US)

(73) Assignee: World Medical Manufacturing Corporation, Sunrise, FL (US)

(*) Notice: Subject to any disclaimer, the term of this patent is extended or adjusted under 35 U.S.C. 154(b) by 0 days.

(21) Appl. No.: 09/257,757

(22) Filed: Feb. 25, 1999

Related U.S. Application Data (60) Provisional application No. 60/076,383, filed on Feb. 26, 1998.

(51) Int. Cl.[7] ....................................................... A61F 2/06
(52) U.S. Cl. .......................................... 623/1.16; 623/1.23
(58) Field of Search ................................. 623/1.11, 1.12, 623/1.13, 1.14, 1.15, 1.16, 1.17, 1.18, 1.2, 1.21; 606/108, 191, 194, 195

(56) References Cited

U.S. PATENT DOCUMENTS

| | | |
|---|---|---|
| 3,625,745 * | 12/1971 | Wright et al. ................ 117/93.31 |
| 4,512,338 | 4/1985 | Balko et al. . |
| 4,580,568 | 4/1986 | Gianturco . |
| 4,651,738 | 3/1987 | Demer et al. . |
| 4,665,918 | 5/1987 | Garza et al. . |
| 4,875,480 | 10/1989 | Imbert . |
| 4,990,151 | 2/1991 | Wallstén . |
| 5,035,706 | 7/1991 | Giantureo et al. . |
| 5,064,435 | 11/1991 | Porter . |
| 5,092,877 | 3/1992 | Pinchuk . |
| 5,104,399 | 4/1992 | Lazarus . |
| 5,158,548 | 10/1992 | Lau et al. . |
| 5,195,058 | 3/1993 | Simon . |
| 5,201,757 | 4/1993 | Heyn et al. . |
| 5,242,399 | 9/1993 | Lau et al. . |
| 5,275,622 | 1/1994 | Lazarus et al. . |
| 5,282,824 | 2/1994 | Giantureo . |
| 5,433,723 | 7/1995 | Lindenberg et al. . |
| 5,443,477 | 8/1995 | Marin et al. . |
| 5,458,615 | 10/1995 | Klemm et al. . |
| 5,480,423 | 1/1996 | Ravenscroft et al. . |
| 5,484,418 | 1/1996 | Quiachon et al. . |
| 5,489,295 | 2/1996 | Piplani et al. . |
| 5,507,769 | 4/1996 | Marin et al. . |
| 5,549,663 | 8/1996 | Cottone, Jr. . |
| 5,619,891 | 4/1997 | Tiede . |
| 5,626,608 | 5/1997 | Cuny et al. . |
| 5,628,783 | 5/1997 | Quiachon et al. . |
| 5,662,675 | 9/1997 | Stockert et al. . |
| 5,683,449 | 11/1997 | Marcade . |
| 5,713,917 | 2/1998 | Leonhardt et al. . |
| 5,735,873 | 4/1998 | MacLean . |

FOREIGN PATENT DOCUMENTS

| | | |
|---|---|---|
| 0 472 731 A1 | 2/1991 | (EP) . |
| 0 505 686 A1 | 9/1992 | (EP) . |
| 0 508 473 A2 | 10/1992 | (EP) . |
| 0 518 839 A2 | 12/1992 | (EP) . |
| 0 539 237 A1 | 4/1993 | (EP) . |
| 0 732 089 A2 | 9/1996 | (EP) . |

* cited by examiner

Primary Examiner—Henry J. Recla
Assistant Examiner—Vy Q. Bui
(74) Attorney, Agent, or Firm—Sterne, Kessler, Goldst & Fox P.L.L.C.

(57) ABSTRACT

A multi-stage stent graft for implantation into a blood vessel is disclosed. Each stage or layer may comprise radially compressible spring stents with or without a fabric covering, or may comprise a foamed tube. The various stages or layers may also have an adhesive coated thereon. The multi-stage stented graft and the adhesive coatings provide a surface for the in growth of cells and promote healing. Also disclosed is a coaxial delivery system for the delivery and endovascular assembly of the multi-stage stented graft during one trip into the vasculature.

31 Claims, 5 Drawing Sheets

DELIVERY SYSTEM FOR DEPLOYMENT AND ENDOVASCULAR ASSEMBLY OF A MULTI-STAGE STENTED GRAFT

CROSS-REFERENCE TO RELATED APPLICATION

The present application claims priority based on U.S. provisional application Ser. No. 60/076,383, filed Feb. 26, 1998.

BACKGROUND OF THE INVENTION

1. Field of the Invention

The present invention generally relates to the area of blood vessel graft systems. More particularly, the present invention provides a catheter base delivery device for deployment of multi-stage stented grafts comprising multiple coaxial delivery mechanisms. The coaxial delivery device enables the multiple stages of a stented graft to be assembled endovascularly.

2. Description of the Related Art

Aortic aneurysms are a common type of deteriorating disease caused by weakening of the wall of a blood vessel. The weakened wall, under the pressure of flowing blood, balloons outward. Such a deformity in the wall of a blood vessel not only affects its ability to conduct blood but is also potentially fatal if a rupture occurs at the site of the aneurysm.

Traditionally, the treatment for aneurysms entailed removing part or all of the aneurysm and implanting a replacement prosthetic section into the lumen. Alternatively, a synthetic or biomaterial graft is sutured end-to-end completely replacing the excised portion of the blood vessel. However, surgical treatment or removal of the aneurysm involves significant invasive techniques, extended hospitalization and associated risk of complications. Complications include extensive blood loss, respiratory tract infections, wound infections, and renal failure. In addition, the mortality rates (8%) are significant for such surgeries.

A more contemporary method of treatment of aneurysms is to place a graft within the lumen of the weakened blood vessel via a catheter based device. Conventional tubular aortic replacement sections, however, are generally larger in diameter than the femoral artery and therefore can not be inserted through the lumen of the femoral artery. The basic concept of a transluminal placement of an endovascular prosthesis for decreasing risk associated with the surgical repair of aortic aneurysms was proposed by Dotter (1969, *Invest Radiol.* 4:329–332). Since then, several investigators have studies the feasibility of different endovascular devices. For example Lazarus (U.S. Pat. No. 5,669,936) discloses a graft system having a capsule catheter that is deployed after femoral arteriotomy. To date, stent-grafts used clinically for treatment of abdominal and thoracic aortic aneurysms have required 18-F to 30-F delivery systems. The large size of the delivery system necessitated surgical femoral arteriotomy and sometimes retroperitoneal left iliac arteriotomy or distal aorta aortotomy, general anesthesia, and high levels of multidisciplinary cooperation. Occasionally, relatively healthy iliac vessels with large diameters are needed or in patients with highly sclerotic tortuous iliac arteries, angioplasty with or without stenting was necessary for performance of endovascular grafting. None of the clinically used devices is suitable for percutaneous insertion; all require a femoral arteriotomy because of their size.

Recently, a catheter based system for the delivery of grafts for repair of aortic aneurysms was disclosed in U.S. Pat. Nos. 5,713,917 and 5,591,195. The system includes a single stage graft comprised of two Nitinol springs. The two Nitinol springs are in physical communication with each other via a Nitinol connecting bar and are embedded in graft material at each end and covered completely by material so as to prevent direct exposure to bodily fluids or tissues. The graft is deployed by using an elongated sheath introducer having an axially extending sheath passage for receiving the graft and maintaining it in a compressed condition. A flexible push rod around the insertion catheter and within the sheath passage is used to push the graft out of the sheath during deployment.

In theory, one way to decrease the size of an endovascular device is to deploy the stented graft as separate parts. However, none of the delivery devices available are suitable for delivery of a multi-stage stented graft by a single percutaneous insertion. There is thus, an ongoing need for graft delivery devices for treatment of aneurysms which requires minimal preparation and hospitalization.

SUMMARY OF THE INVENTION

The present invention provides a multi-stage stented graft that is easily introduced and implanted by percutaneous insertion for the treatment of aneurysms, and which circumvents the need for suturing or stapling to the wall of the blood vessel. The various stages of the stented graft are assembled endovascularly. Accordingly, it is an object of the invention to provide a multi-stage stented graft for implantation into blood vessels.

Another object of the present invention is to provide a multi-stage stented graft that does not have any barbs or hooks for anchoring to the wall of the blood vessel.

Still another object of the present invention is to provide a delivery device for a multi-stage stented graft that requires a single percutaneous insertion.

Yet another object of the present invention is to provide a method for deployment of a multi-stage stented graft using a multiple coaxial delivery device, wherein the stented graft is assembled endovascularly from the multiple stages.

A still further object of the present invention is that the stented graft serves as a substrate for the growth of cells, lining the lumen of the blood vessels in the area of an aneurysm.

These and other aspects of the present invention will become more apparent to those skilled in the art by reference to the following description and to the appended drawings.

DETAILED DESCRIPTION OF THE INVENTION

Since endovascular stented grafts must meet certain strength and durability requirements, the goal of reducing their size profile by decreasing the size of their components is limited. By assembling the components of a stented graft endovascularly, the size of the delivery device is reduced without compromising flexibility. In that respect, the first embodiment of a stented graft of the present invention will be described in detail herein as a two-stage device. However, the present invention is not intended to be so limited and those skilled in the art after having read this specification will readily recognize that two or more stages are within the scope of the present invention. A delivery device for the stented graft is also described. The delivery device enables the stented graft to be introduced into the vasculature through a single percutaneous insertion for subsequent endovascular assembly.

Figure 1:
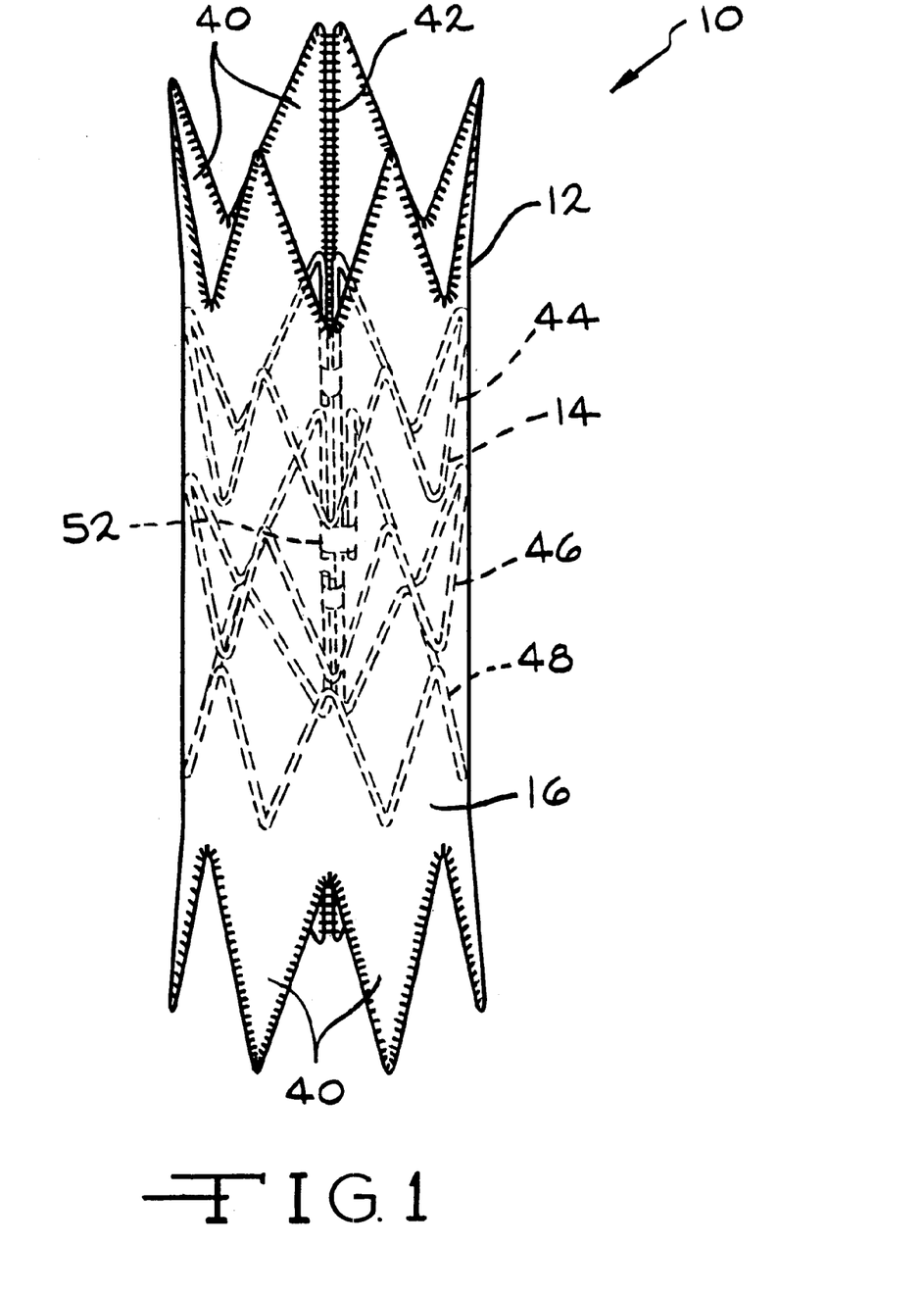
FIG. 1 is a perspective view of a two-stage stented graft 10 of the present invention.
Figure 2A:
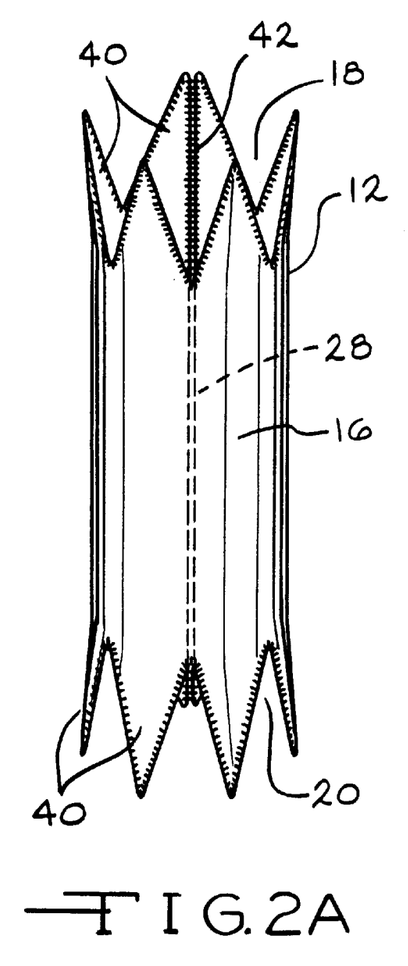
FIG. 2A is a perspective view of a first stage anchoring stent 12 of the two-stage stented graft shown in FIG. 1.
Figure 2B:
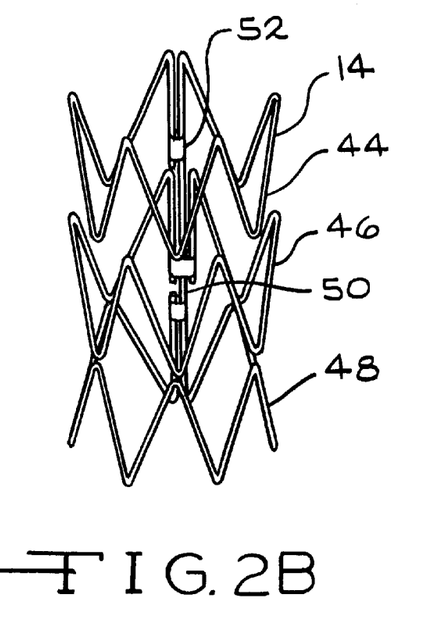
FIG. 2B is a perspective view of a second stage scaffolding stent 14 of the two-stage stented graft shown in FIG. 1.
Figure 2C:
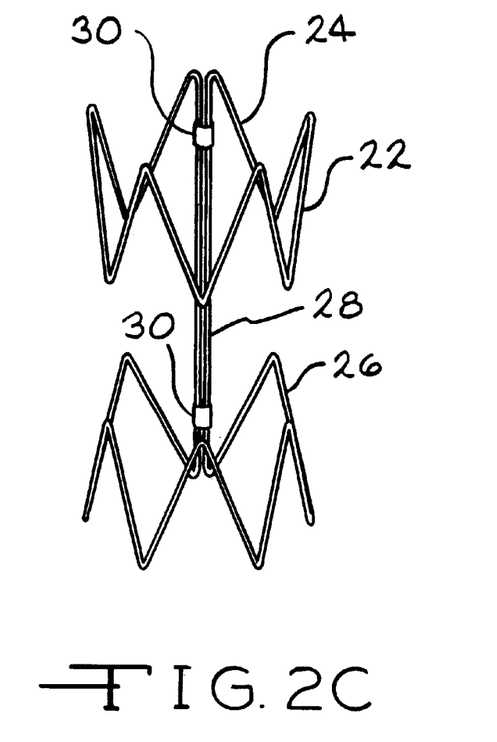
FIG. 2C is a perspective view of the supporting frame 22 of the first stage of the stented graft shown in FIG. 1.

Turning now to the drawings, FIG. 1 shows a fully assembled two-stage stented graft 10 according to the present invention comprising a first stage anchoring stent 12 (FIG. 2A) and a second stage scaffolding stent 14 (FIG. 2B). The anchoring stent 12 comprises a tubular graft 16 having an annular side wall extending to opposed open ends 18 and 20 and a support frame 22 (FIG. 2C). The synthetic material for the tubular graft 16 is pliable enough to substantially conform to the interior surface of a blood vessel being treated. Suitable synthetic materials include, but are not limited to, woven polyester, polytetrafluoroethylene (PTFE), microporous urethane, nylon and lycra. A preferred fabric material is polyester.

Figure 2D:
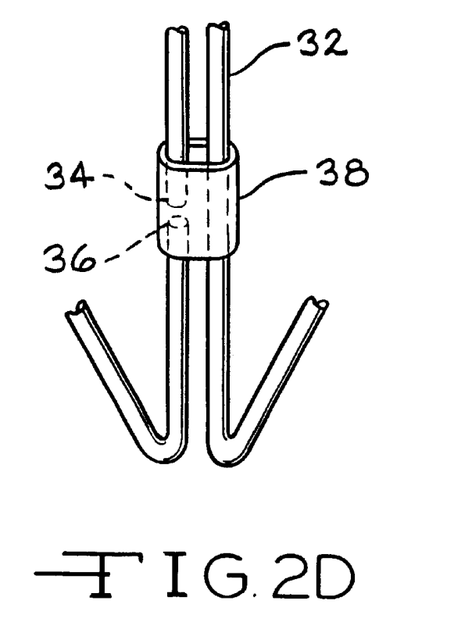
FIG. 2D is a magnified view of a portion of the supporting frame 22 shown in FIG. 2C illustrating the use of a single Nitinol wire for creating the frame.

The support frame 22 comprises a spaced apart first support stent 24 and a second support stent 26 connected to each other by a longitudinal bar 28. If desired, more than one connecting bar is provided. The stents 24 and 26 and the connecting bar 28 can be made as separate parts that are subsequently secured to each other by bands 30 or by welding and the like. If desired, the first and second support stents 24, 26 and the intermediate connecting bar 28 can be made of a single wire 32 that is bent or otherwise formed to shape with its terminal ends 34 and 36 (shown in dashed lines in FIG. 2D) disposed proximate to each other and secured in place by a metal band 38. The ends of the wire 32 can also be welded together to complete the construction. In one embodiment of the present invention, the stage one anchoring stent 12 has the first support stent 24 located at one of the open ends 18 of the tubular graft 16 while the second support stent 26 is located at the other open end 20 with the connecting bar 28 extending therebetween.

In that respect, the tubular graft 16 is initially provided as a sheet or cloth of the synthetic material cut to shape having a plurality of spaced apart flaps or petals 40 extending from each end. The synthetic graft material is formed into the tubular shape by sewing or otherwise securing the sides together along a seam 42. The flaps 40 are sized to cover the peaks and troughs of the respective support stents 24 and 26. The tubular graft 16 is then secured to the support frame 22 by sewing the flaps 40 to cover the peaks and troughs of the first and second stents 24 and 26. Examples of methods of sewing the stents within the graft material are disclosed in U.S. Pat. No. 5,713,917 to Leonhardt et al., which patent is hereby incorporated by reference.

The second stage of the two-stage stented graft 10, termed the scaffolding stent 14, is also made of a plurality of radially compressible spring stents, for example spring stents 44, 46 and 48 connected by connecting bars 50. The scaffolding stent 14 preferably fits longitudinally between the first and second stents 24 and 26 of the first stage anchoring stent 12. The spring stents 44, 46 and 48 and the connecting bars 50 may be made as a unitary member from one wire in a similar manner as the support frame 22 shown in FIG. 2C or the scaffolding stent 14 may be made of separate parts secured together by bands 52, welds and the like. The scaffolding stent 14 may be uncovered or it may be enclosed in a thin polyester covering similar to the tubular graft 16. While not intending to be bound by any particular theory, it is believed that covering both the support frame 22 and the scaffolding stent 14 with, for example, a synthetic material decreases the permeability of the stented graft 10 for abdominal aortic aneurysm treatment and the like. It is important to note that neither the support frame 22 of the anchoring stent 12 or the inner scaffolding stent 14 are equipped with barbs.

In one embodiment, the first and second serpentine stents 24 and 26 and the intermediate connection bar 28 comprising the support frame 22 of the first stage anchoring stent 12 and the second stage scaffolding stent 14 are made of the nickel-titanium alloy Nitinol. Nitinol is a biologically inert alloy which possesses special shape-memory properties. The alloy is made of approximately equal amounts of nickel and titanium. The shape-memory properties of Nitinol enable the various stents to be initially fabricated into a desired shape and configuration and then, just prior to deployment, collapsed into a shape that fits inside the respective catheters of the delivery device of the present invention for transport through the vasculature. When the stented graft 10 is positioned at the location of a damaged portion of the vasculature, such as an aortic aneurysm and the like, the various Nitinol stents are re-deformable into their initial fabricated configurations. In that respect, Nitinol is an alloy typically stable at room and body temperature, but that can be stressed to lose its malleability and then permanently revert to its initially fabricated configuration. The transition temperature of the alloy is controlled by varying the composition and processing of the alloy, as is well known by those skilled in the art.

In another embodiment of the present invention, a photopolymerization technique is used to treat the synthetic material of the tubular graft 16. While not intending to be, bound by any particular theory, it is believed that photopolymerization makes the surface of the synthetic material conducive to bonding of proteins which are necessary to create a collagen rich surface thereon. This enables a thinner, higher porosity fabric to be utilized without bleed-through and also promotes healing. In addition, cryogenically preserved biological materials, for example, veins including umbilical cord veins, can also be used in lieu of the synthetic graft material. Further, selection of the synthetic graft material depends upon the site of implantation. For example, polyester (Dacron) is preferred for the aortic wall which experiences a higher pressure change than for example, the iliac artery, where, PTFE is the preferred material.

In another embodiment of the present invention, the stented graft comprises three stages. In the three stage embodiment, the total thickness is about 0.18 mm measuring in a radial direction extending from the longitudinal axis of the stented graft, with each stage layer being about 0.06 mm thick. The second stage comprises the scaffolding stent 14 having multiple stents connected by a connecting bar. The longitudinal dimensions of the second stage scaffolding stent are such that when it is deployed within the support frame 22 of the anchoring stent 12, the scaffolding stent 14 fits into the space between the first and second support stents 24, 26 of the first stage. The distance between each of the five stents comprising the support frame 22 and the scaffolding stent 14 in the assembled stented graft 10 is approximately 5 mm.

The third stage is similar to the first stage and comprises spaced apart first and second support stents connected to each other by a connecting bar. The third stage does not require a tubular graft, although if desired, one can be provided. The third stage fits inside the second stage with the first or upper support stent spanning between and partially overlapping the first support stent 22 of the anchoring stent 12 and the first spring stent 44 of the scaffolding stent 14 while the second or lower support stent spans between and partially overlaps the second support stent 26 of the first stage and the third stent 48 of the scaffolding stent. That way, the third spring stage provides additional supporting structure to the stented graft of the present invention to insure an open and unobstructed lumen therethrough. A further embodiment has the first support stent of the third stage intermediate, but not overlapping the support stent 22, and the spring stent 44, and the second stent intermediate, but not overlapping the support stent 26 and the spring stent 48.

The second stage, which forms the backbone of the assembled graft, may be bare or covered with a synthetic fabric. The fabric covering the various stages may be made of stretchable or non-stretchable materials. In one embodiment, the synthetic fabric covering the first stage is made of a stretchable material enabling the first and second support stents to conform to the inner diameter of the wall of the vessel being repaired to prevent any leaks around the edges of the graft. The second and the third stages are preferably made of non-stretchable material to provide strength around the area of the aneurysm. When assembled, the first stage forms the outermost layer, the second stage forms the middle layer and the third stage forms the innermost layer and is exposed to the lumen of the vessel.

Figure 4A:
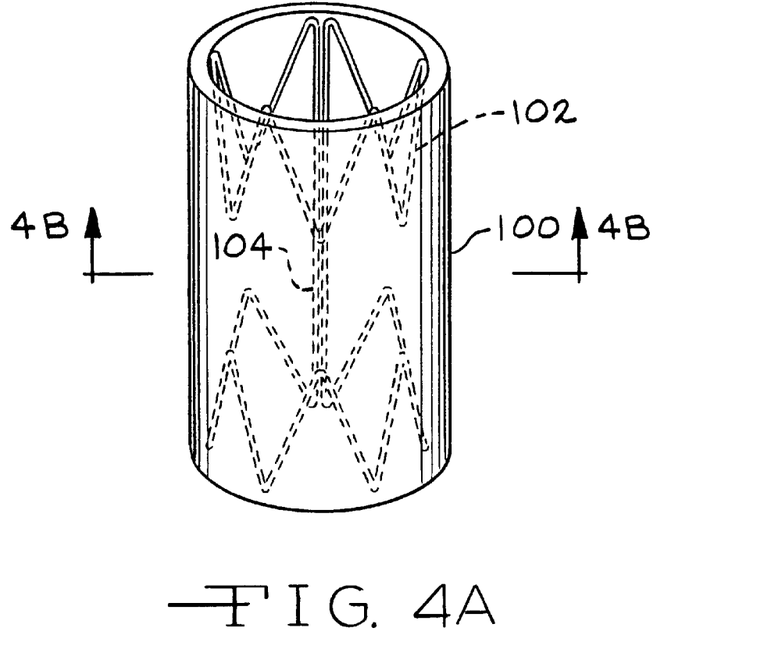
FIG. 4A is a perspective view of a hollow foamed tube 100.
Figure 4B:
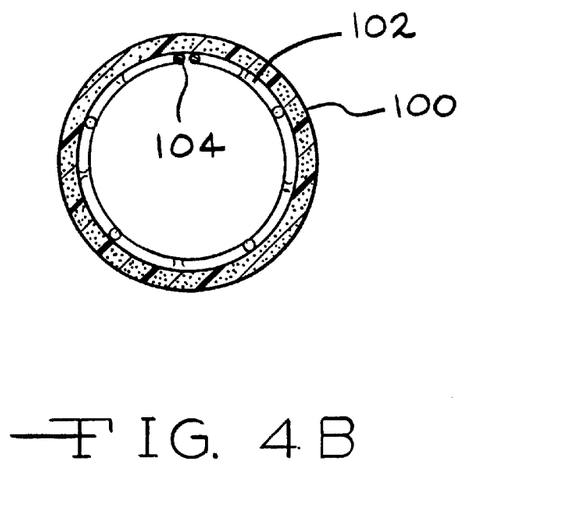
FIG. 4B is a cross-sectional view along line 4B—4B of FIG. 4A.

Another embodiment according to the present invention comprises a three-stage stented graft wherein the first stage is formed by a hollow foamed tube 100 (FIG. 4A) of a closed cell thermoplastic material, as shown in FIG. 4B. It is preferable to have at least one stent 102 provided at the distal open end of the foamed tube to enable easy release of the tube during deployment. More preferably, a stent 102 is provided at each end with at least one connecting wire extending therebetween. The longitudinal support may be a Nitinol wire extending along the length of the foamed tube. The second stage is similar to the support frame 22 of the first stage and comprises two spaced apart support stents and a connecting bar. The third stage is a scaffolding stent similar to the second stage shown in FIG. 2B and comprises multiple connected spring stents that fit between the first and the second support stents of the second stage. If a fourth stage is provided, it is similar to the previously described second stage support frame.

In another embodiment of the present invention, a light activated adhesive is coated between the layers or stages of the stented graft. Suitable adhesives include fibrin glue and isobutyl 2 cyanoacrylate. For example, in the previously described two-stage and three-stage stented grafts, fibrin glue is coated on the external surface of the scaffolding stent 14. The adhesive may be released in vivo as described in the previously referenced U.S. Pat. No. 5,713,917 to Leonhardt et al. In a three-stage or a four-stage stented graft comprising an outer foam layer, the fibrin glue is preferably also applied to the top and bottom portions on the external surface of the foam layer so as to form a tight seal with the wall of the blood vessel. While not intending to be bound by any particular theory, it is believed that the multiple layers provide means for the in growth of cells from the blood vessel wall into the graft. The fibrin coating facilitates the attachment and growth of the cells thus strengthening the graft.

The multi-stage stented grafts of the present invention may be deployed using delivery devices of the type shown and described in the previously referenced U.S. Pat. Nos. 5,713,917 to Leonhardt et al. and U.S. Pat. No. 5,591,195 to Taheri et al., which is hereby incorporated herein by reference. Using those delivery devices, the various stages of the stented graft 10 can be deployed in the artery using successive trips into the vasculative. If delivered separately, it is preferable that all of the stages are deployed without delay, otherwise thrombosis may occur between the graft material and aortic wall as well as intraluminally between the pleats of the partially expanded graft material. A clot formation may decrease the lumen of the graft itself, be a source of distal embolization and jeopardize patency of aortic side branches, which is critically important for treatment of thoracic aortic aneurysms. Recatheterization of the lumen of the graft material is time consuming and may even cause the migration of the previously deployed part.

Figure 3:
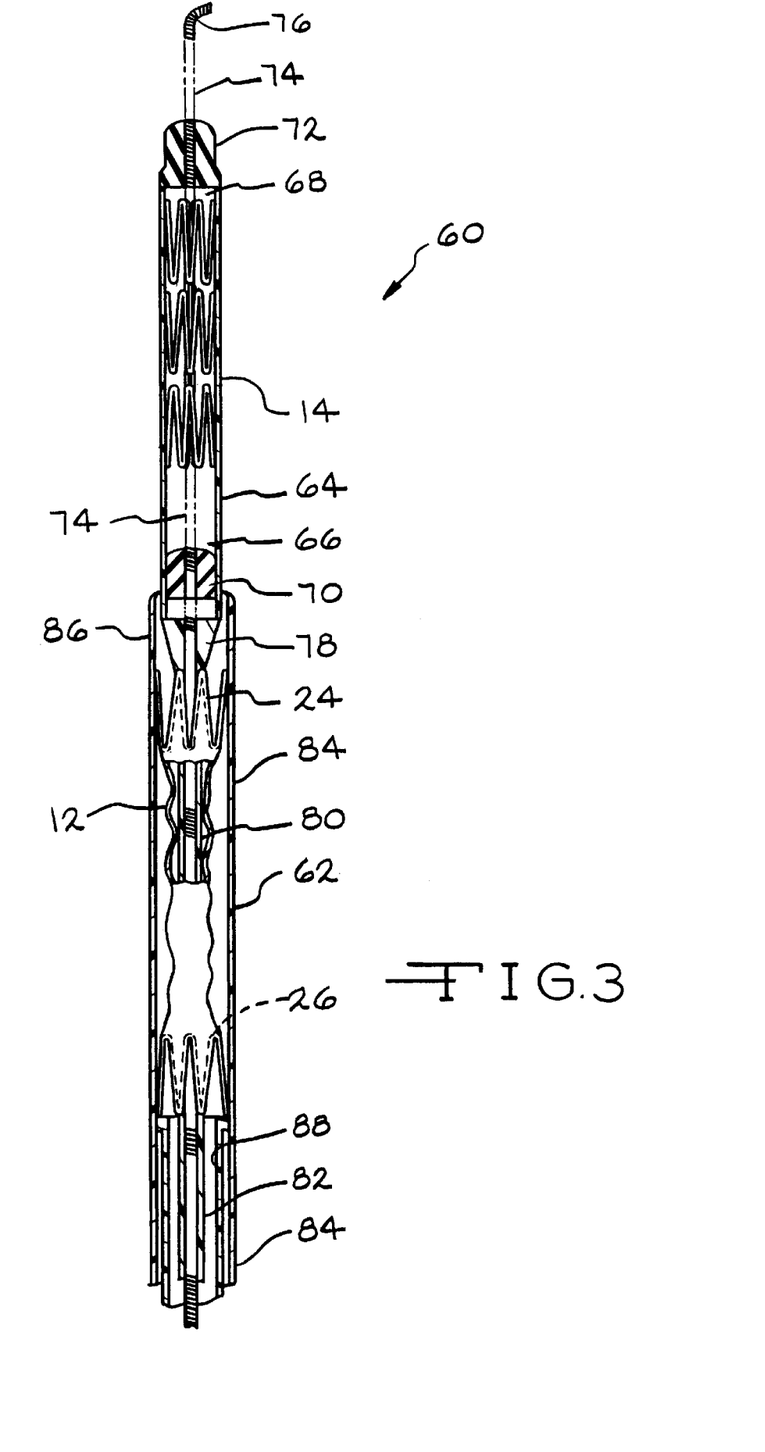
FIG. 3 is a perspective view of a portion of the delivery device for the two-stage stented graft of the present invention.

As shown in FIG. 3, the various embodiments of the stented grafts 10 may also be delivered using a coaxial delivery device 60 of the present invention. Since the stented graft 10 has multiple stages, the size of the delivery device 60 provides for delivery of the various stages of the stented graft 10 through the vasculature and deployment at the treatment site without making multiple entries into the vasculature.

The size of the delivery device needed for placement of a self-expanding stented graft made of serpentine or Z-shaped undulations is determined by several factors. One is the required amount of radial force exerted by the stent. It is known that the radial force of a stent is an increased by increasing the size of the stent wire and/or the number of bends (Fallone et al, 1988, *Invest. Radiol.* 23:370–376). This means that a stent made of a large diameter wire or having an increased number of bends requires a larger delivery device because the compressed diameter of the stent is also increased. Another factor influencing the required size of the delivery device is the diameter of the recipient blood vessel. To increase the unconstrained diameter of a serpentine or Z-shaped stent, more terminal bends must be added which in turn increases the compressed diameter of the stent. The thickness of the covering material itself has a substantial impact on the compressed diameter of the stented graft and, therefore, the size of the delivery sheath. Finally, the coefficient of friction between the graft and the delivery sheath also affects the required size of the delivery device. Friction is influenced by the graft material, the radial force of the stents, and the length of the stent framework. An increased coefficient of friction may necessitate use of a larger delivery device.

Also described is a method of deployment and endovascular assembly of the two-stage stented graft 10. The double coaxial device 60 comprises two independent first and second coaxial delivery sheaths. The first or proximal sheath 62 provides for the deployment of the first stage anchoring stent 12 shown in FIG. 2A, while the distal or second sheath 64 provides for deployment of the scaffolding stent 14 within the lumen of the deployed anchoring stent. Accordingly, the scaffolding stent 14 is housed inside of the second sheath 64 having a cylindrically shaped side wall extending to opposed open ends 66 and 68. In the assembled delivery device, the open ends 66, 68 are closed by respective stoppers 70 and 72 fixedly mounted on the pusher/holder wire 74. The outer diameter of the second sheath 64 is preferably equal to or smaller than 10-F. The pusher/holder wire 74 is provided having a length sufficient to extend outside the vasculature for manipulation by a physician.

The scaffolding stent 14 surrounds the pusher/holding wire 74 intermediate the stoppers 70, 72 with the second sheath 64 housing the scaffolding stent, supported on the stoppers, which are in a moveable relationship with the second sheath. The distal end of the pusher/holding wire 74 is equipped with a short flexible angled tip 76 to facilitate manipulation within the vasculature. The proximal open end 66 of the second sheath 64 further supports a frusto-conically shaped member 78 that tapers downwardly and inwardly toward the pusher/holder wire 74 and the first sheath 62 of the delivery device 60 to form into a small caliber catheter 80. The frusto-conical member 78 is separate from stopper 70 and is preferably a tapered portion of the second sheath 64 that forms into the catheter 80. The catheter 80 surrounds the pusher/holder wire 74 in a closely-spaced relationship and extends to a proximal end 82 adjacent to a proximal end 84 of the first sheath 62.

The proximal end 66 of the second sheath 64 is received inside the distal open end 86 of the first sheath 62 and in a movable relationship therewith. The anchoring stent 12 is housed inside the first sheath 62 in a surrounding relationship with the catheter 80. The anchoring stent 12 is retained in this position by the frusto-conical member 78 and a pusher tube 88 sized to movably fit inside the first sheath 62.

To assemble the delivery device 60 carrying the disassembled stented graft 10, the catheter 80 is moved through the lumen of the anchoring stent 12 with the first serpentine stent 24 of the support frame 22 adjacent to the frusto-conical member 78. The first sheath 62 is then moved over the anchoring stent 12. The scaffolding stent 14 is positioned on the pusher/holder wire 74 intermediate the stoppers 72, 74 and the catheter 80 including the frusto-conical member 78 and the second sheath 64 are moved down the pusher/holder wire 74 until the distal open end 68 of the second sheath 64 abuts the distal stopper 72. The scaffolding stent 14 and the second sheath 64 are now coaxial with the pusher/holder wire 74. In this position, the first sheath 62, anchoring stent 12 and the catheter 80 are coaxial with the pusher/holder wire 74 and the distal open end 86 of the E first sheath 62 surrounds the proximal end 64 of the second sheath 64. Finally, the pusher tube 88 is moved over the pusher/holder wire 74 until its distal end is coaxial with and intermediate the distal open end 86 of the first sheath 62 and the proximal end 82 of the catheter 80.

For delivery and deployment of the multi-stage stented graft 10, the delivery device 60 is inserted percutaneously into a blood vessel. After guiding the delivery device 60 to the desired position, the successive stages of the stented graft 10 are deployed.

First, the first sheath 62 is moved in a proximal direction while the pusher tube 88 and the pusher/holder wire 74 remain stationary. This causes the anchoring stent 12 to deploy with the support stents 24 and 26 of the support frame 24 expanding to the size of the lumen of the vessel being treated. Preferably the anchoring stent 12 is of a length sufficient to span a damaged area of the blood vessel with the support stents 24, 26 located on opposed sides thereof. The first sheath 62 and the pusher tube 88 are then moved in a proximal direction so that they will not interfere with deployment of the scaffolding stent 14.

Next, the scaffolding stent 14 is moved in a proximal direction until it is centered between the support stents 24, 26 of the anchoring stent 12. The scaffolding stent 14 is now deployed by moving the catheter 80 in a proximal direction until the scaffolding stent 14 abuts the stationary stopper 70. The catheter 80 is connected to the second sheath 64 by the frusto-conical member 78 and proximal movement of catheter 80 results in proximal movement of the second sheath 64 and the associated scaffolding stent 14. After proper positioning of the scaffolding stent 14 is confirmed by an imaging technique, the second sheath 64 is moved in a proximal direction to completely unhouse the scaffolding stent 14 which deploys inside the anchoring stent 12.

In that respect, it has been determined that if each of the anchoring stent 12 and the scaffolding stent 14 are deployed inside of the vasculature alone they will each exert a radial force of about 200 units of force, for example. When the scaffolding stent 14 is deployed inside the anchoring stent 12, as described herein, the combined radial force of the two forming the stented graft is at least about 80% of their combined radial force. This increased radial force is provided without decreasing fatigue life.

Another aspect of the present invention is that when the scaffolding stent is deployed inside the anchoring stent, it is preferred to have the peaks or points of the various stents in a non-aligned relationship as determined in a longitudinal direction. This provides for increased point contact with the inside of the vasculature to increase and enhance the sealing effect of the stented graft 10.

While the method of deploying the stented graft 10 has been described with respect to a two-stage stent, the present invention should not be so limited. The stented graft can be provided with three or more stages deployed one inside the other by housing each inside a sheath that is selectively movable to deploy each stage one at a time in a manner similar to that described with the two-stage stent 10.

It is appreciated that various modifications to the invention concepts described herein may be apparent to those skilled in the art without departing from the spirit and scope of the present invention as defined by the hereinafter appended claims.

What is claimed is:

1. A stent device, which comprises:
   a) a support frame having a first support stent spaced apart from a second support stent, wherein said first support stent is connected to said second support stent by at least one connecting wire;
   b) a tubular graft comprising a graft material formed into a tubular shape, wherein said tubular graft is disposed to surround a portion of both said first support stent and said second support stent; and
   c) a scaffolding stent separate from and unconnected to said support frame and positioned within said tubular graft intermediate said first support stent and said second support stent.

2. The stent device of claim 1 wherein said graft material is a synthetic material selected from the group consisting of polyester, polytetrafluoroethylene, microporous urethane, nylon, and lycra.

3. The stent device of claim 1 wherein said graft material is characterized as having been subjected to a photopolymerization process.

4. The stent device of claim 1 wherein said graft material is a cryogenically preserved biological material.

5. The stent device of claim 1 wherein said graft material is an umbilical cord vein.

6. The stent device of claim 1 wherein said support frame and said scaffolding stent are of Nitinol.

7. The stent device of claim 1 wherein said first support stent and said second support stent and said connecting wire of said support frame are a unitary member.

8. The stent device of claim 1 wherein said scaffolding stent comprises at least two stents connected together.

9. The stent device of claim 1 wherein said graft material includes a plurality of spaced apart flaps.

10. The stent device of claim 9, wherein said first support stent and said second support stent include peaks and troughs located at ends of said first support stent and said second support stent, wherein said flaps are oriented to cover said peaks.

11. The stent device of claim 1 wherein said scaffolding stent is enclosed in a thin covering.

12. The stent device of claim 1 further comprising:
  d) a third stage stent, placed within both said support frame and said scaffolding stent to overlap both said support frame and said scaffolding stent.

13. The stent device of claim 1 wherein said scaffolding stent includes an adhesive applied thereto to facilitate attachment to said graft material.

14. The stent device of claim 1, further comprising a second tubular graft comprising a second graft material formed into a tubular shape, wherein said second tubular graft is disposed to surround a portion of said scaffolding stent.

15. The stent device of claim 14, wherein said second tubular graft material is less permeable than said tubular graft material surrounding a portion of both said first support stent and said second support stent.

16. The stent device of claim 14, wherein said second tubular graft material is a different material than said tubular graft material surrounding a portion of both said first support stent and said second support stent.

17. The stent device of claim 16, wherein said second tubular graft material is stretchable and said tubular graft material surrounding a portion of both said first support stent and said second support stent is non-stretchable.

18. The stent device of claim 1, wherein said graft material is fixed to said first support stent and said second support stent by sewing.

19. The stent device of claim 1, wherein said connecting wire longitudinally connects said first support stent and said second support stent.

20. The stent device of claim 1, wherein said connecting wire and said first support stent and said second support stent are comprised of a single wire having terminal ends, wherein said terminal ends are secured in place by a metal band.

21. A stent comprising:
  a) a hollow foamed tube;
  b) a support frame having a first support stent spaced apart from a second support stent, said first support stent and said second support stent being connected to each other by at least one connecting wire and disposed within said hollow foamed tube; and
  c) a scaffolding stent separate from and unconnected to said support frame, said scaffolding stent being positioned intermediate said first support stent and said second support stent of said support frame in said hollow foamed tube.

22. The stent of claim 21 wherein said scaffolding stent comprises at least two stents connected together.

23. The stent of claim 21 further comprising a third scaffolding stent, disposed within both said support frame and said scaffolding stent to overlap at least a portion of both said support frame and said scaffolding stent.

24. The stent of claim 21 wherein an adhesive is applied to an external surface of said hollow foamed tube to form a tight seal with the wall of a blood vessel.

25. The stent of claim 24 wherein said adhesive is fibrin glue.

26. The stent of claim 21, wherein said first support stent, said second support stent, and said connecting wire of said support frame are of a unitary member.

27. The stent of claim 21, wherein said hollow foamed tube is formed of a closed cell thermoplastic material.

28. The stent of claim 21, wherein said connecting wire longitudinally connects said first support stent and said second support stent.

29. The stent of claim 28, wherein said connecting wire is a Nitinol wire.

30. The stent of claim 21, wherein said connecting wire and said first support stent and said second support stent are comprised of a single wire having terminal ends, wherein said terminal ends are secured in place by a metal band.

31. A stent device comprising:
  a) a tubular graft having a first open end and a second open end, said graft being made of a graft material,
  b) a support frame having a first support stent disposed at and fixed to an annular wall of said tubular graft at a first end of said tubular graft, said support frame having a second support stent disposed at and fixed to said annular wall of said tubular graft at a second end of said tubular graft, wherein said first support stent is spaced apart from said second support stent and wherein said first support stent is connected to said second support stent by at least one connecting wire; and
  c) a scaffolding stent separate from and unconnected to said support frame and positioned within said tubular graft intermediate said first support stent and said second support stent.

* * * * *